United States Patent [19]

Paulus et al.

[11] 4,395,274

[45] Jul. 26, 1983

[54] MICROBICIDAL AGENT AND ITS USE

[75] Inventors: Wilfried Paulus; Hermann Genth, both of Krefeld, Fed. Rep. of Germany

[73] Assignee: Bayer Aktiengesellschaft, Leverkusen, Fed. Rep. of Germany

[21] Appl. No.: 52,872

[22] Filed: Jun. 28, 1979

[30] Foreign Application Priority Data

Mar. 10, 1979 [DE] Fed. Rep. of Germany ....... 2909550

[51] Int. Cl.³ ..................... A01N 25/00; A01N 31/08; A01N 43/50; A01N 43/52
[52] U.S. Cl. .......................................... 71/67; 71/92; 71/122; 424/273 B; 424/346; 424/347
[58] Field of Search ..................... 424/273 B, 346, 347; 71/67, 92, 122

[56] References Cited

U.S. PATENT DOCUMENTS 3,010,968 11/1961 Loux ................................... 548/306
3,417,185 12/1968 Herschler ........................... 424/287
3,657,443 4/1972 Klopping ........................... 548/306

OTHER PUBLICATIONS

The Merck Index, 9th Ed. (1976) (3047) and (7110).

*Primary Examiner*—Allen J. Robinson
*Attorney, Agent, or Firm*—Sprung, Horn, Kramer & Woods

[57] ABSTRACT

Synergistic combinations of active compounds consisting of benzimidazolyl-alkyl-carbonates and (2,2'-dihydroxy-5,5'-dichlor)-diphenyl-methane or 2-hydroxydiphenyl have a strong activity against micro-organisms. The combination can be employed e.g. for protecting industrial materials against microbicidal decomposition.

14 Claims, No Drawings

MICROBICIDAL AGENT AND ITS USE

The invention relates to new synergistic combinations of active compounds consisting of benzimidazolyl-alkyl-carbamates and (2,2'-dihydroxy-5,5'-dichloro)-diphenyl-methane or 2-hydroxydiphenyl.

It is known from German Offenlegungsschrift No. 1,620,175 to use benzimidazolyl-alkyl-carbamates as fungicides in plant protection and for providing industrial materials with fungicidal protection. It is also known that (2,2'-dihydroxy-5,5'-dichloro)-diphenyl-methane and 2-hydroxy-diphenyl have a microbicidal activity ((Chemie der Pflanzenschutz- und Schädlingsbekämpfungsmittel (Chemistry of plant protection agents and pesticides), Vol 3, pg. 287, Springer Publishers 1976).

Microbicial agents have been found which contain
(a) benzimidazolyl-alkyl-carbamates of the formula

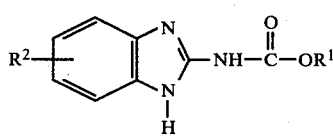

in which
$R^1$ denotes an alkyl radical with 1 to 4 carbon atoms, which is optionally substituted by the radical $-OR^3$, in which $R^3$ stands for an alkyl radical with 1 to 4 carbon atoms or for the phenyl radical, and
$R^2$ denotes hydrogen, an alkyl radical with 1 to 4 carbon atoms, halogen or the nitro group, and
(b) a phenolic compound of the formula

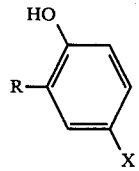

in which
R stands for the phenyl radical or the 2-hydroxy-5-chlorobenzyl radical and
X denotes hydrogen or chlorine.

Alkyl radicals ($R^1$, $R^2$ and $R^3$) may be straight-chained or branched hydrocarbon radicals, such as methyl, ethyl, propyl, isopropyl, butyl or isobutyl, in particular methyl.

Halogens ($R^2$) may be fluorine, chlorine, bromine or iodine, in particular chlorine.

The following benzimidazolyl-alkyl-carbamates may be mentioned as examples: benzimidazolyl-methyl-carbamate, benzimidazolyl-ethyl-carbamate, 5-ethyl-benzimidazolyl-ethyl-carbamate, benzimidazolyl-isopropyl-carbamate, 4-ethyl-benzimidazolyl-isopropyl-carbamate, 4-propyl-benzimidazolylisopropyl-carbamate, 4-butyl-benzimidazolyl-isopropyl-carbamate, 4-isobutyl-benzimidazolyl-isopropyl-carbamate, benzimidazolyl-ethylmethoxy-carbamate, 4-ethyl-benzimidazoly-ethylmethoxy-carbamate, 5-ethyl-benzimidazolyl-ethylmethoxy-carbamate, benzimidazolyl-ethylethoxy-carbamate, benzimidazolyl-ethylpropoxy-carbamate, benzimidazolyl-ethylphenoxy-carbamate, 4-ethyl-benzimidazolyl-ethylphenoxy-carbamate and 5-ethyl-benzimidazolyl-ethylphenoxy-carbamate.

The preferred benzimidazolyl-alkyl-carbamate is benzimidazolyl-methyl-carbamate.

It is of course also possible to use mixtures of various benzimidazolyl-alkyl-carbamates.

The preparation of benzimidazolyl-alkyl-carbamates is known (U.S. Pat. No. 3,010,968).

The compounds of formula II can also be combined with the benzimidazolyl carbamates in the form of salts, preferably alkali salts, such as sodium salts and potassium salts.

Preferred compounds of the formula II are 2-hydroxydiphenyl and (2,2'-dihydroxy-5,5'dichloro)-diphenyl-methane.

The active compound (2,2'-dihydroxy-5,5'-dichloro)-diphenyl-methane is prepared by treating 1 mol 4-chlorobenzene with 0.5 mol formaldehyde in aqueous solution adding sulphuric acid at 50° C. to 65° C.

The condensation of cyclohexanone forms cyclohexenyl-cyclohexanone and the catalytic dehydrogenation of this produces 2-hydroxy-diphenyl.

The weight ratios of the active compounds in the combinations of active compounds can vary within relatively wide ranges.

In general there are 1 to 25 parts by weight, and preferably 2 to 15 parts by weight, of (2,2'-dihydroxy-5,5'-dichloro)-diphenyl-methane or 2-hydroxy-diphenyl per part by weight of benzimidazolyl-alkyl-carbamate.

Combinations of 1 part by weight of benzimidazolyl-methyl-carbamate and 2 to 10 parts by weight of (2,2'-dihydroxy-5,5'-dichloro)-diphenyl-methane or 2-hydroxy-diphenyl are particularly effective.

The particle size of the active compounds according to the invention is variable within wide limits. In general, active compounds with a particle size of 100 to 350 microns, and preferably from 150 to 300 microns, are employed.

The active compounds according to the invention can also be employed in the form of their alkali salts.

The combinations of active compounds according to the invention display a strong activity against micro-organisms. Examples of micro-organisms which may be mentioned are bacteria, yeasts, fungi and algae.

Examples of bacteria, yeasts and fungi which may be mentioned are *Bacillus subtilis, Bacterium vulgare, Escherichia coli, Staphylococcus aureus, Alternaria tenuis, Aspergillus niger, Candida albicans, Candida crusei, Chaetomium globosum, Coniophora cerebella, Lentinus tigrinus, Penicillium glaucum, Polyporus versicolor, Pullularia pullulans, Rhizopus nigricans, Trichoderma viride, Trichophyton pedis, Torula utilis.*

Examples of algae which may be mentioned are: *Euglena gracilis Klebs, Oscillatoria geminata Meneghini, Phaedoactylum tricornutum Bohlin* and *Stichococcus bacillaris Naegili.*

The invention relates to combinations of active compounds for protecting industrial materials against microbial decomposition. Industrial materials are, for example, adhesives, glues, paper and cardboard, textiles, leather, wood, paints, plasters and the contents of packages which can be damaged or destroyed by microbial action. The mixtures of the active compounds according to the invention are particularly suitable for preserving glues, textiles, paper and wood.

The new combinations of active compounds can be converted into the customary formulations, such as, for example, solutions, suspensions, pastes and powders.

The new combinations of active compounds can be used as such, in the form of their formulations and in the use forms prepared therefrom. They are used in the customary manner, for example by homogeneous distribution in the material to be protected or by impregnating, coating or spraying industrial materials.

The amount of the combinations of active compounds employed depends on the nature and the incidence of the microorganisms, on the germ count and on the medium. For use, the optimum amount to be employed can be determined by test series in each case. In general, however, it is sufficient to employ 0.05 to 1% of the mixtures of active compounds.

The action of benzimidazolyl-alkyl-carbamates and (2,2'-dihydroxy-5,5'-dichloro)-diphenyl-methane and 2-hydroxy-diphenyl in single compounds against micro-organisms is limited, there are gaps in their spectrum of activity. As a solution to this problem a combination of active compounds consisting of benzimidazolyl-methyl-carbamate and 3,5-dimethyl-tetrahydro-1,3,5-thiadiazine-2-thione is already known (German Published Specification No. 2,150,219). A disadvantage of this known combination of active compounds is that 3,5-dimethyl-tetrahydro-1,3,5-thiadiazine-2-thione, as a formaldehyde depot substance, is only moderately stable. Similar disadvantages apply in the case of the combinations of active substances (2,2'-dihydroxy-5,5'-dichloro)-diphenyl-methane or 2-hydroxy-diphenyl and benzylalkoholmono(poly)-hemiformaldehyde (Proceed. 3rd Int. Biodegrad. Symp. 1975, Appl. Science Publishers Ltd. London (1975), pp. 1075 to 1082).

The combinations of active compounds according to the invention are, on the other hand, distinguished by their stability and advantageously have a wide spectrum of activity. The use of mixtures of active compounds according to the invention does not produce concentrations in effluents which hinder the biological clarification.

Surprisingly the microbicidal activity of the combinations of active compounds according to the invention is considerably higher than the sum of the actions of the individual active compounds. Thus, a synergistic effect exists.

It is advantageously possible, with the aid of the combinations of active compounds according to the invention, to produce microbicide-containing starch size (dry) without any losses of active compound and the disagreeable odours and environmental pollution associated with these losses, as is the case, for example, with agents based on pentachlorophenol. The risk of discoloration and the odour and decomposition involved with the drying of alkaline glue slurries also limit the usability of dithiocarbamates such as zinc-dimethyl-dithiocarbamate or tetramethylthiuram disulphide.

The combinations of active compounds according to the invention can also advantageously be used in the production of antimicrobial paper material, such as soap wrappings and crepe towelling, for which, besides having a successful and broad antimicrobial action the active compounds have to be colourless, odourless, heat stable, insoluble in water, resistant to hydrolysis, of low volatility and stable in colour. Such requirements are not fulfilled by halogenated phenolic active compounds, which are volatile in water vapour and soluble in water, nor by agents based on dithiocarbamate which can cause reductions in the degree of whiteness.

The spectrum of activity of the combinations of active compounds according to the invention includes blue stain fungi (e.g. *Pullularia pullulans*), fungi producing mildews (e.g. *Chaetomium globosum*), but also lignicidal fungi (e.g. *Coniophora cerebella*). The combinations of active compound are therefore suitable for the protection of sawn wood; here, in addition to the broad spectrum of activity, the low toxicity of the combinations of active compounds ($LD_{50}$ oral approx. 3000 mg/kg rats) is particularly advantageous. By way of comparison: The $LD_{50}$ oral of sodium pentachlorophenolate is 270 mg/kg rats.

The combinations of active compounds according to the invention make it possible, advantageously, to replace the microbicidal agents available hitherto by more effective agents and to reduce the amount of biocide necessary for combating micro-organisms.

EXAMPLE 1

Symbols:
A = (2,2'-dihydroxy-5,5'-dichloro)-diphenyl-methane
B = benzimidazolyl-methyl-carbamate In order to demonstrate the synergistic action the minimum inhibitory concentrations (MIC) of A and B in agar culture media are determined. The MIC values of A and B are compared with the MIC values of mixtures A/B.

The synergism is determined according to the method described by Kull et al (F. C. Kull, P. C. Eismann, H. D. Sylvestrowicz, R. L. Mayer, Applied Microbiol. 9, 538 to 541, 1961). The following symbols apply here:

$$\frac{Q_A}{Q_a} + \frac{Q_B}{Q_b} = X$$

$X = 1$ denotes additivity
$X > 1$ denotes antagonism
$X < 1$ denotes synergism
$Q_a$ = concentration of compound A, which represents the MIC
$Q_b$ = concentration of compound B, which represents the MIC
$Q_A$ = the amount of compound A in the concentration of A/B, which prevents the growth of microbes
$Q_B$ = the amount of compound B in the concentration of A/B which prevents the growth of microbes.

The result is recorded in the following table.

TABLE

| Wt. ratio A/B | MIC in mg/l | $Q_a$ | $Q_A$ | $Q_b$ | $Q_B$ | X |
|---|---|---|---|---|---|---|
| Test organism *Aspergillus niger* | | | | | | |
| 100/0 | 20 | 20 | 20 | 2,5 | — | 1 |
| 20/1 | 2 | " | 1,9 | " | 0,1 | 0,13 |
| 10/1 | 2 | " | 1,8 | " | 0,2 | 0,16 |
| 6/1 | 2 | " | 1,7 | " | 0,3 | 0,20 |
| 2/1 | <1 | " | <0,7 | " | <0,3 | <0,17 |
| 1/1 | <1 | " | <0,5 | " | <0,5 | <0,23 |
| 1/2 | <1 | " | <0,3 | " | <0,7 | <0,29 |
| 0/100 | 2,5 | " | — | " | 2,5 | 1 |
| Test organism *Coniophora cerebella* | | | | | | |
| 100/0 | 10 | 10 | 10 | 2000 | — | 1 |
| 20/1 | <1 | " | <0,95 | " | <0,5 | <0,1 |
| 10/1 | <1 | " | <0,9 | " | <0,1 | <0,1 |
| 6/1 | <1 | " | <0,86 | " | <0,14 | <0,1 |
| 2/1 | 2 | " | 1,4 | " | 0,6 | 0,14 |
| 1/1 | 5 | " | 2,5 | " | 2,5 | 0,25 |
| 1/2 | 5 | " | 1,7 | " | 3,3 | 0,17 |
| 0/100 | 2000 | " | — | " | 2000 | 1 |
| Test organism *Chaetomium globosum* | | | | | | |
| 100/1 | 50 | 50 | 50 | 0,4 | — | 1 |
| 20/1 | 3,5 | " | 0,33 | " | 0,17 | 0,49 |

TABLE-continued

| Wt. ratio A/B | MIC in mg/l | $Q_a$ | $Q_A$ | $Q_b$ | $Q_B$ | X |
|---|---|---|---|---|---|---|
| 10/1 | <1 | " | <0,9 | " | <0,1 | <0,27 |
| 6/1 | <1 | " | <0,86 | " | <0,14 | <0,36 |
| 2/1 | <1 | " | <0,7 | " | <0,3 | <0,76 |
| 0/100 | 0,4 | " | — | " | 0,4 | 1 |
| Test organism *Alternaria tenuis* | | | | | | |
| 100/0 | 20 | 20 | 20 | 5000 | — | 1 |
| 10/1 | <20 | " | <18,2 | " | <1,8 | <0,91 |
| 6/1 | <20 | " | <17,3 | " | <2,7 | <0,87 |
| 1/1 | <20 | " | <10 | " | <10 | <0,5 |
| 1/2 | 50 | " | 16,7 | " | 33,3 | <0,84 |
| 0/100 | 5000 | " | — | " | 5000 | 1 |
| Test organism *Trichoderma vivide* | | | | | | |
| 100/0 | 50 | 50 | 50 | 2,5 | — | 1 |
| 20/1 | 35 | " | 33,3 | " | 1,7 | 0,7 |
| 6/1 | 7,5 | " | 6,4 | " | 1,1 | 0,57 |
| 2/1 | 2 | " | 1,3 | " | 0,7 | 0,31 |
| 1/1 | 1 | " | 0,5 | " | 0,5 | 0,21 |
| 1/2 | 1 | " | 0,7 | " | 1,3 | 0,53 |
| 0/100 | 2,5 | " | — | " | 2,5 | 1 |
| Test organism *Pullularia pullulans* | | | | | | |
| 100/0 | 20 | 20 | 20 | 0,25 | — | 1 |
| 10/1 | <1 | " | <0,9 | " | <0,1 | <0,45 |
| 6/1 | <1 | " | <0,86 | " | <0,14 | <0,6 |
| 0/100 | 0,25 | " | — | " | 0,25 | 1 |

EXAMPLE 2

Symbols:
A=(2,2'-dihydroxy-5,5'-dichloro)-diphenyl-methane
B=benzimidazolyl-methyl-carbamate A dry size with a starch base is produced from a glue slurry which contains 0.3% of a mixture with A/B=6/1, based on the amount of dried glue. The dry size is diluted with water in a ratio of 1:25, in comparison with one free of microbicides. After 3-day storage at room temperature the size free of microbicides is thinly liquid and unusable (bacterial count after 7 days: $2.4 \times 10^6$/g), whereas the size containing the agent according to the invention does not exhibit any loss in viscosity (bacterial count after 7 days: nil).

1000μ layers of the microbicide-containing size are spread on to filter paper. The test specimens are placed on to nutrient media which are contaminated with moulds (*Aspergillus niger, Chaetomium globosum, Trichoderma viride*). Storage took place at room temperature.

Under these conditions size layers free of microbicides are completely covered in fungi after 1 week; the above-mentioned size layers, however, remain free from fungi, i.e. they are mould-resistant.

By way of comparison a size slurry, which contains, based on dry size, 0.45% of 3-methyl-4-chloro-phenol and 0.15% of zinc dimethyldithiocarbamate, was prepared and tested as described above. Results: no decrease in viscosity; poor mould-resistance.

EXAMPLE 3

Symbols:
A=(2,2'-dihydroxy-5,5'-dichloro)-diphenyl-methane
B=benzimidazolyl-methyl-carbamate Based on the weight of the paper (90 to 100 g/m²) 0.5% of A/B=6/1 is homogeneously mixed under a pulp (density 1%, pH value 4.8) having the following composition:

39.9% of bleached sulphite cellulose
39.9% of bleached birch sulphate cellulose
0.2% of a commercially available clearing agent
2% of a commercially available rosin size
15% clay
3% alum.

The paper produced from this pulp is mould-resistant; the system for feeding in the pulp remains free of fungus during the paper production so that the use of other antifungal agents is unnecessary.

The mould resistance and the antimicrobial activity of the soap-wrapping paper obtained in this manner is tested in the following way:

Circular paper test specimens (diameter 4 cm) are placed in a nutrient medium in Petri dishes, the medium having previously been infested with the test fungi *Chaetomium globosum Kunze* and *Aspergillus niger*. After 8 to 14 days of storage at 30° C. and 90% to 95% relative atmospheric moisture paper free of active compounds is completed overgown by the test fungi, whereas the paper produced as described above is still free from fungi even under these extreme conditions; also, inhibitory areas form around the test specimens.

If the test specimens are coated with a nutrient medium layer which is contaminated with bacteria (*Staphylococcus aureus*) after 3 to 5 days' storage under the same conditions the antibacterial action of the paper becomes visible in the form of a growth-free zone, which forms over and surrounding the test specimens.

If, however, as is customary, owing to the lack up until now of usable alternatives, 0.5% of sodium pentachlorophenolate (related to the weight of the paper) is added to the pulp, losses of active compound amounting to more than 50% occur (approx. 25% are found in the effluent and approx. 25% in the outgoing air). The consequences are: effluent problems (the effluent is toxic to fish), discharged air problems (disagreable odours, mucosal irritation, poor mould-resistance).

EXAMPLE 4

Symbols:
A=(2,2'-dihydroxy-5,5'-dichloro)-diphenyl-methane
B=benzimidazolyl-methyl-carbamate A commercially available wall raw-paper is coated with a starch size which contains, based on the dry size, 0.3% of A/B=6/1. The weight of the paper is 80 g/m². The layer of adhesive is 8 g/m² (after drying). The self-adhesive wall raw-paper produced in this way is mould-resistant—as is shown by the following test.

Test specimens (diameter 4.5 cm) are placed on agar nutrient media in Petri dishes which are previously infested with moulds (e.g. *Trichoderma viride, Chaetomium globosum Kunze, Aspergillus niger*) which have been isolated from mould wallpapers. After one week of storage at 30° C. and 90% to 95% relative atmospheric moisture the test specimens are still free from fungi. Under the same conditions and in the same time a wall raw-paper which has a layer of adhesive free from active compound becomes completely covered with a growth of the test fungi.

EXAMPLE 5

Symbols:
A=(2,2'-dihydroxy-5,5'-dichloro)-diphenyl-methane
B=benzimidazolylmethylcarbamate A mixed culture of green, blue, brown and siliceous algae (*Stichococcus bacillaris Naegeli, Euglena gracilis Klebs, Chlorella pyrenoidosa Chick, Phormidium foredarum Gromont, Oscillatoria geminata Meneghini* and *Phaedodactylum tricornutum Bohlin*) is added, whilst bubbling through air, to Allen's nutrient solution (Arch. Mikrobiol. 17, 34 to 53, (1952)) which contains 0.2 g ammonium chloride, 4.0 g sodium nitrate, 1.0 g dipotassium hydrogen phosphate, 0.2 g calcium chloride, 2.05 g magnesium sulphate and 0.02 g iron chloride per 4 l sterilized water. After 2 weeks the nutrient solution is coloured a deep greeny blue owing to the intensive growth of algae. The destruction of the algae after the addition of the active compounds according to the invention can be recognized by the decolouring of the nutrient solution.

A mixture according to the invention consisting of 6 parts by weight of (2,2'-dihydroxy-5,5'-dichloro)-diphenyl-methane and 1 part by weight of benzimidazolyl-methyl-carbamate in a concentration of 50 mg/l kills the above-mentioned algae.

EXAMPLE 6

Symbols:
A=2-hydroxy-diphenyl
B=benzimidazolyl-methyl-carbamate

In order to demonstrate the synergistic activity the same procedure is followed as in Example 1.

The results are recorded in the following table.

TABLE

| Wt. ratio A/B | MIC in mg/l | $Q_A$ | $Q_a$ | $Q_B$ | $Q_b$ | X |
|---|---|---|---|---|---|---|
| Test organism *Aspergillus niger* | | | | | | |
| 100/0 | 50 | 50 | 50 | — | 2,5 | 1 |
| 20/1 | 7,5 | 6,64 | " | 0,36 | " | 0,28 |
| 10/1 | <1 | <0,9 | " | <0,1 | " | <0,1 |
| 6/1 | <1 | <0,86 | " | <0,14 | " | <0,1 |
| 2/1 | <1 | <0,67 | " | <0,33 | " | <0,16 |
| 1/1 | <1 | <0,5 | " | <0,5 | " | <0,2 |
| 1/2 | <1 | <0,33 | " | <0,67 | " | <0,28 |
| 0/100 | 2,5 | — | " | 2,5 | " | 1 |
| Test organism *Coniophora cerebella* | | | | | | |
| 100/0 | 50 | 50 | 50 | — | 2000 | 1 |
| 20/1 | 50 | 47,6 | " | 2,4 | " | 0,95 |
| 10/1 | 50 | 45,5 | " | 4,5 | " | 0,91 |
| 6/1 | 50 | 42,9 | " | 7,1 | " | 0,86 |
| 2/1 | 50 | 33,3 | " | 16,7 | " | 0,67 |
| 1/1 | 50 | 25 | " | 25 | " | 0,51 |
| 1/2 | 100 | 33 | " | 67 | " | 0,69 |
| 0/100 | 2000 | — | " | 2000 | " | 1 |
| Test organism *Chaetomium globosum* | | | | | | |
| 100/0 | 50 | 50 | 50 | — | 0,4 | 1 |
| 20/1 | 2 | 1,9 | " | 0,1 | " | 0,29 |
| 10/1 | <1 | <0,9 | " | <0,1 | " | <0,27 |
| 6/1 | <1 | <0,85 | " | <0,14 | " | <0,38 |
| 2/1 | <1 | <0,67 | " | <0,33 | " | <0,84 |
| 0/100 | 0,4 | — | " | 0,4 | " | 1 |
| Test organism *Trichoderma viride* | | | | | | |
| 100/0 | 75 | 75 | 75 | — | 2,5 | 1 |
| 20/1 | 10 | 9,52 | " | 0,48 | " | 0,32 |
| 10/1 | 5 | 4,54 | " | 0,46 | " | 0,25 |
| 6/1 | 5 | 4,29 | " | 0,71 | " | 0,34 |
| 2/1 | <1 | <0,67 | " | <0,33 | " | <0,14 |
| 1/1 | <1 | <0,5 | " | <0,5 | " | <0,21 |
| 1/2 | <1 | <0,33 | " | <0,67 | " | <0,27 |
| 0/100 | 2,5 | — | " | 2,5 | " | 1 |
| Test organism *Pullularia pullulans* | | | | | | |
| 100/0 | 50 | 50 | 50 | — | 0,25 | 1 |
| 20/1 | 3,5 | 3,33 | " | 0,17 | " | 0,75 |
| 10/1 | <1 | <0,9 | " | <0,1 | " | <0,42 |
| 6/1 | <1 | <0,86 | " | <0,1 | " | <0,58 |
| 0/100 | 0,25 | — | " | 0,25 | " | 1 |

What we claim is:

1. A composition for killing bacteria, algae, fungi and yeast which comprises a bacteriacidally, fungicidally, algaecidally or yeasticidally effective amount of;
(a) a benzimidazolyl-alkyl-carbamate of the formula

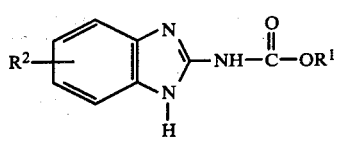

(I)

in which
R$^1$ denotes an alkyl with 1 to 4 carbon atoms, and
R$^2$ denotes hydrogen or an alkyl with 1 to 4 carbon atoms and
(b) a phenolic compound selected from the group consisting of (2,2'-dihydroxy-5,5'-dichloro) diphenylmethane and 2 hydroxy diphenyl which is present in an amount of 0.5 to 20 parts by weight per part by weight of said carbamate.

2. A composition according to claim 1 wherein said phenolic compound is present in an amount of 2 to 15 parts by weight per part by weight of said carbamate.

3. A composition according to claim 1 wherein said phenolic compound is present in an amount of 2 to 10 parts by weight per part by weight of said carbamate.

4. An composition according to claim 1 wherein said phenolic compound is (2,2'-dihydroxy-5,5'-dichloro)diphenylmethane.

5. An composition according to claim 1 wherein said phenolic compound is 2-hydroxydiphenyl.

6. A composition according to claim 1, wherein R$^1$ denotes methyl or ethyl.

7. A composition according to claim 1, wherein R$^2$ denotes hydrogen.

8. A composition according to claim 6, wherein R$^2$ denotes hydrogen.

9. A process for killing a bacteria, algae, fungus or yeast which comprises contacting the bacteria, algae, fungi or yeast with a bacteriacidally, fungicidally, algaecidally or yeasticidally effective amount of the composition of claim 1.

10. A process according to claim 9 wherein said bacteria, fungus or algae is in an industrial material.

11. A process according to claim 9 wherein said industrial material is a glue, a textile, paper or wood.

12. A process for protecting an industrial material against microbial decomposition due to bacteria, algae, fungi or yeast which comprises contacting said industrial material with a bacteriacidally, fungicidally, algaecidally or yeasticidally effective amount of the composition of claim 1.

13. A process according to claim 9 wherein said baceria, yeasts and fungi are selected from the group consisting of *Bacillus subtilis, Bacterium vulgare, Escherichia coli, Staphylococcus aureus, Alternaria tenuis, Aspergillus niger, Candida albicans, Candida crusei, Chaetomium globosum, Coniophora cerebella, Lentinus tigrinus, Penicillium glaucum, Polyporus versicolor, Pullularia pullulans, Rhizopus nigricans, Trichoderma viride, Trichophyton pedis* and *Torula utilis.*

14. A process according to claim 9 wherein said bacteria, yeast, algae or fungi is selected from the group consisting of *Aspergillus niger, Coniophora cerebella, Chaetomium globosum, Alternarida tenuis, Trichoderma viride* and *Pullularia pullulans.*

* * * * *

UNITED STATES PATENT AND TRADEMARK OFFICE
CERTIFICATE OF CORRECTION

PATENT NO. : 4,395,274

DATED : July 26, 1983

INVENTOR(S) : Wilfried Paulus et al

It is certified that error appears in the above-identified patent and that said Letters Patent is hereby corrected as shown below:

Column 7, line 45, delete "<0,85" and insert --<0.86--.

Column 8, line 63, "Alternarida" should read -- Alternaria --.

Signed and Sealed this

Sixth Day of December 1983

[SEAL]

Attest:

GERALD J. MOSSINGHOFF

*Attesting Officer*   *Commissioner of Patents and Trademarks*